(12) United States Patent
Profet

(10) Patent No.: US 10,342,823 B2
(45) Date of Patent: *Jul. 9, 2019

(54) TOPICAL AND ORAL FORMULATIONS COMPRISING TAURINE AND MAGNESIUM FOR THE PREVENTION AND TREATMENT OF ACNE

(71) Applicant: Margaret Jean Profet, Manhattan Beach, CA (US)

(72) Inventor: Margaret Jean Profet, Manhattan Beach, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/787,565

(22) Filed: Oct. 18, 2017

(65) Prior Publication Data

US 2018/0036340 A1 Feb. 8, 2018

Related U.S. Application Data

(63) Continuation of application No. 15/179,815, filed on Jun. 10, 2016, now Pat. No. 9,795,633.

(60) Provisional application No. 62/180,842, filed on Jun. 17, 2015.

(51) Int. Cl.
| | | |
|---|---|---|
| *A61K 33/08* | (2006.01) | |
| *A61K 31/185* | (2006.01) | |
| *A61K 33/06* | (2006.01) | |
| *A61K 9/00* | (2006.01) | |
| *A61K 9/06* | (2006.01) | |
| *A61K 45/06* | (2006.01) | |
| *A61K 8/00* | (2006.01) | |

(52) U.S. Cl.
CPC ............... *A61K 33/08* (2013.01); *A61K 8/00* (2013.01); *A61K 9/0014* (2013.01); *A61K 9/0053* (2013.01); *A61K 9/06* (2013.01); *A61K 31/185* (2013.01); *A61K 33/06* (2013.01); *A61K 45/06* (2013.01)

(58) Field of Classification Search
CPC combination set(s) only.
See application file for complete search history.

(56) References Cited

U.S. PATENT DOCUMENTS

| | | | |
|---|---|---|---|
| 4,199,601 A | 4/1980 | Durlach | |
| 4,545,977 A | 10/1985 | Gaull | |
| 5,776,504 A | 7/1998 | McCarty | |
| 5,876,757 A | 3/1999 | McCarty | |
| 5,962,517 A | 10/1999 | Murad | |
| 6,558,656 B2 | 5/2003 | Mann | |
| 7,258,875 B2 | 8/2007 | Chiou | |
| 7,955,610 B2 | 6/2011 | Tanthapanichakoon et al. | |
| 9,795,633 B2* | 10/2017 | Profet | A61K 33/08 |
| 2004/0039042 A1 | 2/2004 | Fleming | |
| 2004/0214891 A1 | 10/2004 | Marcinkiewicz et al. | |
| 2005/0008684 A1 | 1/2005 | Herdeis et al. | |
| 2006/0193922 A1 | 8/2006 | Neikrug | |
| 2010/0172993 A1 | 7/2010 | Singh et al. | |
| 2013/0337086 A1 | 12/2013 | Goolsbee et al. | |
| 2014/0121188 A1 | 5/2014 | Tamarkin et al. | |

FOREIGN PATENT DOCUMENTS

| | | |
|---|---|---|
| EP | 2318011 | 5/2011 |
| WO | WO 2016/003798 A1 | 1/2016 |

OTHER PUBLICATIONS

Ancient Minerals Magnesium Gel, http://www.ancient-minerals.com/products/magnesium-gel; Original publication date unknown; Version printed on Jun. 16, 2016; 2 pages.
Adams, Joseph A., "Kinetic and Catalytic Mechanisms of Protein Kinases," Chemical Reviews, 101, 2271-2290, 2001.
Browne, H., et al., Retinoids and pregnancy: an update, The Obstetrician & Gynaecologist, vol. 16, pp. 7-11, 2014.
Chang, Rong-Kun, et al., "Generic Development of Topical Dermatologic Products: Formulation Development, Process Development, and Testing of Topical Dermatologic Products," The AAPS Journal, vol. 15, No. 1, Jan. 2013.
Clearface AC, Natural Acne Supplement, http://www.myclearface.com/pages/the-product; Original publication date unknown; Version.
Drug Topics, "Overview of Pharmaceutical Excipients Used in Tablets and Capsules", Oct. 24, 2008. Accessed Mar. 5, 2016. http://drugtopics.modernmedicine.com/drug-topics/news/modernmedicine/modern-medicine-news/overview-pharmaceutical-excipients-used-tablets; 12 pages.
Hoang, Minh-Hien, et al., "Taurine is a liver X receptor—α ligand and activities transcription of key genes in the reverse cholesterol transport without inducing hepatic lipogenesis," Molecular Nutrition & Food Research, 56, 900-911, 2012.
International Search Report and Written Opinion dated Sep. 7, 2016 in International Application No. PCT/US2016/037050 filed Jun. 10, 2016; 19 pages.
Li, J., et al., Lubricants in Pharmaceutical Solid Dosage Forms, Lubricants, vol. 2, pp. 21-43, 2014.
Marcinkiewicz, Amy, et al., "The Phosphorylation of Serine 492 of Perilipin a Directs Lipid Droplet Fragmentation and Dispersion," The Journal of Biological Chemistry, vol. 281, No. 17, 11901-11909, Apr. 28, 2006.
Mag K Taurine, http://www.aor.ca/en/product/mag-k-taurine; Original publication date unknown; Version printed on Jun. 16, 2016; 2 pages.
Magnesium Taurine, http://www.aor.ca/en/product/magnesium-taurine; Original publication date unknown; Version printed on Jun. 16, 2016; 2 pages.

(Continued)

*Primary Examiner* — Aradhana Sasan
(74) *Attorney, Agent, or Firm* — Knobbe, Martens, Olson & Bear, LLP

(57) ABSTRACT

Topical and oral compositions for treating and/or preventing acne are disclosed. The compositions include effective amounts of taurine and magnesium, wherein the effective amounts are sufficient to treat and/or prevent the acne. A method for treating and/or preventing acne in a subject in need thereof is also disclosed. The method includes administering to the subject topical and/or oral compositions including taurine and magnesium in amounts sufficient to treat and/or prevent the acne.

8 Claims, No Drawings

(56) References Cited

OTHER PUBLICATIONS

Mitragotri, Samir, et al., "Overcoming the challenges in administering biopharmaceuticals: formulation and delivery strategies," Nature Reviews Drug Discovery, 13, 655-672, 2014.

Murad, Acne Starter Kit, http://www.sephora.com/acne-starter-kit-P385328; Original publication date unknown; Version printed on Nov. 16, 2015; 2 pages.

Murad, Skin Perfecting Lotion, https://www.murad.com/product/acne-lotion; Original publication date unknown; Version printed on Jun. 17, 2016; 6 pages.

Raphael, Anthony P., et al., "Formulation Design for Topical Drug and Nanoparticle Treatment of Skin Disease," Therapeutic Delivery, 6(2), 197-216, 2015.

Wiesenthal, Alison, et al., "Nanoparticles: small and mighty," International Journal of Dermatology, vol. 50, Issue 3, 247-254, Mar. 2011.

Orthoplex MagTaur Xcell, Australian Register of Therapeutic Goods (ARTG), Public Summary, ARTG Start Date: Dec. 7, 2015, Retrieved: Nov. 19, 2018.

Communication pursuant to Rules 70(2) and 70a(2) EPA, dated Dec. 12, 2018, in European Application No. 16812186.1.

Extended European Search Report dated Dec. 3, 2018 in European Patent Application No. 16812186.1.

\* cited by examiner

TOPICAL AND ORAL FORMULATIONS COMPRISING TAURINE AND MAGNESIUM FOR THE PREVENTION AND TREATMENT OF ACNE

PRIORITY AND CROSS REFERENCE TO RELATED APPLICATIONS

This application is a Continuation Application of U.S. application Ser. No. 15/179,815, filed Jun. 10, 2016, which is to be issued as U.S. Pat. No. 9,795,633 on Oct. 24, 2017, which claims priority to U.S. Provisional Application No. 62/180,842, filed Jun. 17, 2015, the entire disclosures of which are incorporated herein by reference thereto.

BACKGROUND

The present embodiments relate to compositions and methods for the prevention and treatment of acne. In particular, a topical gel, a topical cream and/or an oral supplement comprising taurine and magnesium are disclosed for prevention and/or treatment of acne.

The pilosebaceous units of the skin consist of the sebaceous glands, sebaceous ducts, and their attached hair follicles. Acne (vulgaris) is a disease characterized by a clogging of the skin's pilosebaceous units by the sebum produced by the sebaceous glands. Lipogenesis is lipid production, which occurs in cells of sebaceous glands to produce sebum for the skin, and which can lead to acne when it becomes excessive. Lipid droplets in the sebaceous glands store the lipids produced by the sebaceous glands.

Acne has generally been considered to be an insolvable problem. Acne affects almost all people at some time during life, usually during teenage and young adult years, when sebum production increases in response to an increase in the body of androgen production that typically occurs during these years. Acne is also fairly common in mid-adulthood, and can even occur during early childhood. Acne can become chronic, and can have large negative impact on quality-of-life.

Many topical and oral treatments for acne exist, yet none are generally considered to be cures. In this sense, the field of acne treatment is "crowded art", having only imperfect solutions. Some prescription acne medicines have serious side effects, and so are not considered completely safe (e.g., isotretinoin, which is teratogenic). Thus there has been a long-felt need for a good solution to the problem of acne.

SUMMARY

A composition for treating and/or preventing an acne condition is provided. In some embodiments, the composition comprises an effective amount of taurine and an effective amount of magnesium, wherein the effective amounts of taurine and magnesium are sufficient in combination to treat and/or prevent the acne condition. In some embodiments, the composition is a topical gel or a topical cream. In some embodiments of the composition, the amount of taurine is in a range of about 200 mg to about 2 g per ½ teaspoon of the gel or the cream. In some embodiments of the composition, the amount of magnesium is in a range of about 40 mg to about 400 mg per ½ teaspoon of the gel or the cream. In some embodiments, the composition further comprises a pharmaceutically acceptable carrier. In some embodiments, the composition is an oral supplement. In some embodiments of the composition, the oral supplement is a capsule or a tablet or a powder. In some embodiments of the composition, the amount of taurine is in a range of about 500 to about 3000 mg per capsule or per tablet or per unit dose of powder. In some embodiments of the composition, the amount of magnesium is in a range of about 50 to about 300 mg per capsule or per tablet or per unit dose of powder. In some embodiments, the composition further comprises one or more micronutrients, wherein the one or more micronutrients selected from the group consisting of vitamin D, vitamin A, zinc, and choline may support functions of taurine and magnesium in one or more pilosebaceous units, or wherein the composition further comprises one or more micronutrients, wherein the one or more micronutrients selected from the group consisting of including vitamin B1, vitamin B2, vitamin B3, vitamin B5, vitamin C, vitamin E, vitamin K, Folic Acid, Calcium, Iron, Phosphorous, Iodine, Potassium, Selenium, Manganese, Copper, Inositol, Omega 3 fatty acids, Lycopene, Lutein, and Zeaxanthin may help overall skin functioning.

A method for treating and/or preventing an acne condition in a subject in need thereof is provided. In some embodiments, the method comprises administering to the subject a composition comprising taurine and magnesium in amounts sufficient to treat and/or prevent the acne condition. In some embodiments of the method, administering comprises topically applying the composition in the form of a topical gel or a topical cream. In some embodiments of the method, the amount of taurine is in a range of about 200 mg to about 2 g per ½ teaspoon of the gel or the cream. In some embodiments of the method, the amount of magnesium is in a range of about 40 mg to about 400 mg per ½ teaspoon of the gel or the cream. In some embodiments of the method, administering comprises orally administering the composition in a form of an oral supplement. In some embodiments of the method, the oral supplement is a tablet or a capsule or a powder. In some embodiments of the method, the amount of taurine is in a range of about 500 to about 3000 mg per capsule or per tablet or per unit dose of powder. In some embodiments of the method, the amount of magnesium is in a range of about 50 to about 300 mg per capsule or per tablet or per unit dose of powder. In some embodiments, the method further comprises assessing a severity of the acne, and varying a dose of the composition administered, such that lower dosages are administered in mild cases and higher dosages are administered in severe cases. In some embodiments of the method, the dose is a single daily or a multiple daily dose. In some embodiments of the method, the composition further comprises one or more micronutrients selected from the group consisting of vitamin A, vitamin B1, vitamin B2, vitamin B3, vitamin B5, vitamin B6, vitamin B12, vitamin C, vitamin D, vitamin E, vitamin K, Folic Acid, Biotin, Calcium, Iron, Phosphorous, Iodine, Potassium, Zinc, Selenium, Manganese, Copper, Choline, Inositol, Omega 3 fatty acids, Lycopene, Lutein and Zeaxanthin. In another variation of the method, the administering comprises both topically applying a dose of the composition in the form of a topical gel or a topical cream, and orally administering a dose of the composition in the form of an oral supplement.

DETAILED DESCRIPTION

One reason that the problem of acne has remained unsolved is that many dermatologists have traditionally regarded acne as a normal part of puberty. Evidence has shown, however, that acne is not an inherent part of the human condition, as it does not seem to occur among humans whose diets and ways of life resemble the diets and ways of life to which humans are naturally adapted. Because acne in modern environments occurs extremely commonly, it has not been obvious to dermatologists that the pilosebaceous units have specialized physiological mechanisms whose function is to prevent acne from occurring. Therefore, dermatologists have not identified the mechanisms in the pilosebaceous units that are naturally designed to limit sebaceous oil production and oil build-up and to thereby prevent clogging. Such mechanisms and their biochemical triggers have not been identified before. Therefore, it has not been shown before that these biochemical triggers are particular micronutrients, that chronic insufficiencies of these particular micronutrients can lead to acne, and that supplementation with these micronutrients at certain doses can often reverse the disease of acne.

Embodiments of this disclosure relate generally to the use of taurine and magnesium in combination for the treatment or prevention of acne. The combination therapy may include oral delivery, topical delivery or both oral and topical delivery. A surprising observation is that the dosages of supplemental taurine that are efficacious against acne are much higher than typical dietary dosages of taurine; whereas the dosages of supplemental magnesium that together with taurine are efficacious are in the range of typical dietary dosages. While both taurine and magnesium or derivatives thereof have been used as individual active ingredients in the treatment of acne, the combination has not been used before for acne. Taurine and magnesium have not been identified before as triggering a sequence of lipid-regulating mechanisms in the pilosebaceous units that prevent acne.

US patent publication US20050008684 A1 (Herdeis and Weis) teaches two related taurine derivatives, taurolidine and taurultam, used in pharmaceutical compositions to treat acne; magnesium was not disclosed. U.S. Pat. No. 6,558,656 (Mann) teaches an acne formulation comprising magnesium, as well as many vitamins, minerals, and thymic peptides; no taurine was used. U.S. Pat. No. 4,545,977 (Gaull) teaches an acne formulation comprising taurine, together with isotretinoin, but no magnesium was used. U.S. Pat. No. 5,962,517 (Murad) teaches an acne formulation comprising inter alia magnesium and an amino acid; no taurine is disclosed. Although taurine is an organic acid with an amine group, it is not an amino acid in the strict biochemical sense because it lacks a carboxyl group, nor was it included among the amino acids that Murad disclosed. U.S. Pat. No. 7,955,610 (Tanthapanichakoon et al) discloses an antimicrobial acne treatment that comprises magnesium silicate, but no taurine. U.S. Pat. No. 7,258,875 (Chiou) teaches a topical formulation for treating acne comprising one or more polyvalent metal compounds, including magnesium; no taurine is disclosed. U.S. patent US20040214891 A1 (J. Marcinkiewicz, A. Kasprowicz) discloses a topical acne formulation comprising taurine-bromamine; no magnesium is disclosed. U.S. Pat. No. 5,876,757 A (McCarty) teaches use of magnesium taurate for the treatment of stroke. U.S. Pat. No. 5,776,504 A (McCarty) teaches use of magnesium taurate for prevention and treatment of pre-eclampsia and for acute cardiac conditions. U.S. Pat. No. 4,199,601 A (Durlach) discloses a taurine derivative and divalent metal salts thereof, including magnesium salts for neuromuscular activity reinforcement; neither taurine nor magnesium are disclosed as individual ingredients. European patent EP2318011A2 (Levis) teaches compositions for the treatment of acne comprising taurine together with standard acne medications; no magnesium is disclosed. The product "Magnesium Gel" by Ancient Minerals (accessible on the World Wide Web at ancient-minerals.com) is transdermal magnesium in gel form; it contains no taurine. The product "Magnesium+Taurine" by Advanced Orthomolecular Research (AOR) (accessible on the World Wide Web at aor.ca) is an oral supplement comprising magnesium and taurine for cardiovascular and neurological support. The product is not directed to the treatment of acne. The oral supplement product "Mag-K-Taurine" by AOR provides electrolytes magnesium, potassium, and taurine for the purpose of improving nerve and heart function; it is not a treatment for acne, and does not come in a topical gel/cream form. None of the prior art is based on the unobvious mechanisms of actions of taurine and magnesium in the pilosebaceous units that are presented in the following section.

Taurine and Magnesium—a Combined Role in Sebaceous Gland Lipid Metabolism

Taurine is a free amino acid synthesized by the body as well as obtained in diet through meat, fish, and milk. It is not one of the alpha amino acids which serve as building blocks for proteins. Most commercially available taurine is synthesized in laboratories. Taurine in the sebaceous glands likely helps stop excess lipogenesis, by binding as an inhibitory ligand to the LXR-alpha (liver X receptor-alpha). The LXR-alpha is a receptor that is expressed by many cell types, including cells of the sebaceous glands, and that usually induces lipogenesis when activated by a ligand. The main evidence that taurine halts LXR-alpha-induced lipogenesis is a study by Hoang et al., Molecular Nutrition & Food Research, 56:900-911 (2012) showing experimentally in liver cells in vitro that taurine is a ligand of LXR-alpha that inhibits lipogenesis, resulting in a dose-dependent marked reduction in cellular lipid levels. Taurine is likely to have the same LXR-alpha-related function of reducing lipogenesis in sebaceous glands that it has in liver cells. A reduction of lipogenesis in the sebaceous glands results in a reduction of sebum and consequently less chance of sebum clogging the pilosebaceous units. Taurine thus appears to be part of the regulatory feedback system that keeps sebaceous lipogenesis in check.

Magnesium is a mineral. Magnesium likely helps activate the breakdown of the large lipid droplets in the sebaceous glands/sebaceous ducts via magnesium-activated protein kinase phosphorylation of the lipid droplet surface protein perilipin. This process allows perilipin to direct lipolysis of lipid droplets, fragmenting them into many microlipid droplets and dispersing them. Support for this activity of magnesium comes from the following two pieces of information taken together: protein kinase A phosphorylation of perilipin A has been shown in fat cells to drive the rapid fragmentation and dispersion of lipid droplets (A. Marcinkiewicz et al., Journal of Biological Chemistry, 281:11901-11909 (2006)); magnesium plays an activating role in protein kinase A phosphorylation (Adams, Chemical Reviews, 101: 2271-2290 (2001)). Magnesium likely has the same effect of activating lipolysis of the large perilipin-coated lipid droplets in the sebaceous glands/ducts that it does of the lipid droplets of fat cells. A fragmentation of the large lipid droplets into micro-droplets may help prevent the clogging of the pilosebaceous units.

Taurine and magnesium have been found to work synergistically, in that taurine can facilitate the transport of magnesium across cell membranes. Accordingly, in the human studies described in the EXAMPLES section, the simultaneous use of taurine with magnesium has been found to treat acne much better than either taurine or magnesium used alone.

Topical Compositions Comprising Taurine and Magnesium

In some embodiments, a composition for the prevention and/or treatment of acne is provided. The composition may be a topical gel or a topical cream or an oral supplement. In some embodiments, the composition comprises at least two active ingredients. The active ingredients may be micronutrients. In some embodiments of the composition, the two active ingredients are taurine and magnesium. In some embodiments, one of the two active ingredients is present at a relatively high concentration. In some embodiments, one of the two active ingredients is present at a relatively low concentration. One of the two active ingredients is produced synthetically in the standard ways.

In some embodiments, the subject is in need of a composition to prevent acne. In a variation, a topical composition is administered to the subject. The topical composition administered to the subject may be a topical gel. The topical composition administered to the subject may be a topical cream. In some embodiments, the subject is administered an oral composition. In other embodiments, the subject is in need of one or both of the topical compositions. In another variation, the subject is in need of one or both of the topical compositions and the oral composition. Alternatively, prevention and/or treatment of the acne may be effected by administration of just the oral dosage form.

In some embodiments, the subject is in need of a treatment for acne. The subject is in need of a composition for the treatment for acne. In some embodiments, a topical composition is administered to the subject. The topical composition administered to the subject may be a topical gel. The topical composition administered to the subject may be a topical cream. In some embodiments, the subject is administered an oral composition. In other embodiments, the subject is in need of one or both of the topical compositions. In another variation, the subject is in need of one or both of the topical compositions and the oral composition.

Taurine and magnesium are likely involved in mechanisms that reduce lipogenesis in the sebaceous glands of the skin, and activate the breakdown of large lipid droplets of the sebaceous glands or sebaceous ducts. A topical composition can achieve rapid penetration of taurine and magnesium into skin. Thus, in some embodiments a topical composition is provided. The topical composition comprises taurine and magnesium. In some embodiments, the topical composition comprising taurine and magnesium can achieve rapid penetration of taurine and magnesium into skin. The topical composition may be referred to herein as "topical tau-mag."

In some embodiments, a topical composition for the prevention of acne is provided. In some embodiments, a topical composition for the treatment of acne is provided. In some embodiments, the composition is a topical gel or a topical cream that comprises at least two active ingredients. The two active ingredients may be two micronutrients. In some embodiments, the two micronutrients are taurine and magnesium. In some embodiments, taurine is present in high concentrations and magnesium is present in low concentrations. The taurine may be produced synthetically in the standard ways.

In some embodiments, the dose of taurine is about 3 g per day. The dose of taurine may be from about 0.5 to about 6 g per day. In some embodiments, the dose of taurine is equal to about 0.5, 1, 1.5, 2, 2.5, 3, 3.5, 4, 4.5, 5, 5.5 or 6 g per day or within a range defined by any two of the aforementioned values. The dose of taurine in the topical composition may be greater than about 0.1 g per day and less than about 20 g per day. In another variation, the topical composition comprises taurine in a range of about 200 mg to about 2 g per ½ teaspoon of a topical gel or a topical cream.

The topical composition may additionally comprise a low dose of magnesium. The magnesium in tau-mag may be magnesium citrate, magnesium chloride, magnesium oxide or some other form of magnesium. In some embodiments, the dose of magnesium is about 200 mg per day. In some embodiments, the dose of magnesium is from about 25 to about 500 mg per day. In some embodiments, the dose of magnesium is equal to about 25, 50, 100, 150, 200, 250, 300, 350, 400, 450 or 500 mg per day or within a range defined by any two of the aforementioned values. The dose of magnesium in the topical composition may be greater than about 1 mg per day and less than about 1 g per day. In another variation, the topical composition comprises magnesium in a range of about 40 mg to about 400 mg per ½ teaspoon of a topical gel or a topical cream.

In some embodiments, the topical composition is used for about 1 day to about 21 days. In some embodiments, the topical composition is used for 1, 2, 3, 4, 5, 6, 7, 8, 9, 10, 11, 12, 13, 14, 15, 16, 17, 18, 19, 20 or 21 days or within a range defined by any two of the aforementioned values. In some embodiments, the topical composition is used for about 1 to about 52 weeks. In some embodiments, the topical composition is used for 4, 5, 6, 7, 8, 9, 10, 11, 12, 13, 14, 15, 16, 17, 18, 19, 20, 21, 22, 23, 24, 25, 26, 27, 28, 29 or 30 weeks or within a range defined by any two of the aforementioned values.

The topical composition may be used as divided doses per day. In some embodiments, the topical composition is used as about 2 to about 12 divided doses per day. In some embodiments, the topical composition is used as 2, 3, 4, 5, 6, 7, 8, 9, 10, 11 or 12 divided doses per day or within a range defined by any two of the aforementioned values. In some embodiments, the topical composition is used as multiple doses per day. In some embodiments, the topical composition is used as about 2 to about 12 multiple doses per day. In some embodiments, the topical composition is used as 2, 3, 4, 5, 6, 7, 8, 9, 10, 11 or 12 multiple doses per day or within a range defined by any two of the aforementioned values.

In some embodiments, the age of the subject is from about 10 to about 70 years. The age of the subject may be 10, 15, 20, 25, 30, 35, 40, 45, 50, 55, 60, 65 or 70 years or within a range defined by any two of the aforementioned values. In some embodiments, the age of the subject is lower than about 10 years. In some embodiments, the age of the subject is higher than about 70 years. In some embodiments, the sex of the subject is a male. In some embodiments, the sex of the subject is a female. In some embodiments, the subject has had acne for about 1 day. In some embodiments, the subject has had acne for less than 5 years. In some embodiments, the subject has had acne for about 5 years. In some embodiments, the subject has had acne for more than about 5 years. In some embodiments, the weight of the subject is from about 100 to about 250 lbs. In some embodiments, the weight of the subject is lower than about 100 lbs. In some embodiments, the weight of the subject is higher than about 250 lbs.

In some embodiments, the subject has not tried other acne remedies. In some embodiments, the subject has tried other acne remedies. In some embodiments, the subject has unsuccessfully tried other acne remedies. In some embodiments, the relief from acne from other remedies was less than about 50%. In some embodiments, the relief from acne from other remedies was about 5 to about 50%. In some embodiments, the relief from acne from other remedies was equal to about 5, 10, 15, 20, 25, 30, 35, 40, 45 or 50% or within a range defined by any two of the aforementioned values.

In some embodiments, the relief from acne from topical tau-mag may be about 80 to about 100%. In some embodiments, the relief from acne from topical tau-mag may be equal to about 80, 85, 90, 91, 92, 93, 94, 95, 96, 97, 98, 99 or 100% or within a range defined by any two of the aforementioned values.

In some embodiments, the topical composition additionally may comprise other micronutrients such as vitamins. In some embodiments, the topical composition additionally may comprise other micronutrients such as minerals. In some embodiments, the topical composition additionally may comprise other vitamins and minerals. In some embodiments, the topical composition additionally may comprise one or more micronutrients, wherein the one or more micronutrients is selected from the group consisting of vitamin A, vitamin B1, vitamin B2, vitamin B3, vitamin B5, vitamin B6, vitamin B12, vitamin C, vitamin D, vitamin E, vitamin K, Folic Acid, Biotin, Calcium, Iron, Phosphorous, Iodine, Potassium, Zinc, Selenium, Manganese, Copper, Choline, Inositol, Omega 3 fatty acids, Lycopene, Lutein and Zeaxanthin.

In some embodiments, the subject has mild acne. In some embodiments, the subject has moderate acne. In some embodiments, the subject has severe acne. In some embodiments, the subject has mild-moderate acne. In some embodiments, the subject has moderate-severe acne. In some embodiments, topical tau-mag may be partially effective. In some embodiments, topical tau-mag may be about 80 to about 99% effective. In some embodiments, topical tau-mag is 80, 85, 90, 91, 92, 93, 94, 95, 96, 97, 98 or 99% effective or within a range defined by any two of the aforementioned values. In some embodiments, topical tau-mag is fully effective. In some embodiments, topical tau-mag may be about 100% effective. Topical tau-mag may mitigate scars due to acne. Topical tau-mag may mitigate scars due to mild acne. Topical tau-mag may mitigate scars due to moderate acne. Topical tau-mag may mitigate scars due to severe acne. Scarring from acne may be reduced about 20 to about 80% by topical tau-mag. Scarring from acne may be reduced equal to about 20, 25, 30, 35, 40, 45, 50, 55, 60, 65, 70, 75 or 80% by topical tau-mag or within a range defined by any two of the aforementioned values.

In some embodiments, topical compositions comprising high-dose taurine (about 3 g per day) together with low-dose magnesium (about 200 mg per day) may be very effective against mild-moderate acne, and may be partially effective against severe acne.

In some embodiments, topical compositions comprising high-dose taurine (about 3 g per day, in divided doses) in combination with low-dose magnesium (about 200 mg magnesium per day, in divided doses) may improve mild-moderate acne about 90 to about 100% within about 4 to about 12 weeks.

The formulation may be a topical anti-acne gel/cream. The goal of applying a topical formulation is to achieve rapid penetration of taurine and magnesium into the pilosebaceous units of the skin. Depending on the severity of acne, either an oral formulation or a topical formulation or both an oral and a topical formulation may be used by the subject in need thereof. In some cases, the oral and/or topical formulation may be combined with other micronutrients such as vitamins and/or minerals.

In some variations, topical tau-mag may be a squeezable tube or a jar, of any pharmacological size and dimension, of anti-acne topical gel or cream. In some embodiments, contents of topical tau-mag are taurine, magnesium and a vehicle (pharmaceutical carrier of dermatological agents) gel or cream comprised of inactive ingredients and preferably aqueous-based. For each ½ teaspoon of topical tau-mag gel/cream, the amount of taurine contained in it may be in a range of about 200 mg to about 2 g, and the amount of magnesium contained in it may be in a range of about 20 mg to about 400 mg.

The composition of the vehicle may be selected so as to be easy to apply and remove, be nonirritant, non-allergenic, chemically stable, homogenous, and pharmacologically inert. In some embodiments, vehicle gels/creams such as this are well known in pharmaceutical and aesthetics industries by those skilled in the art of manufacturing gels/creams. In some embodiments, taurine and magnesium would be mixed into the vehicle to form the gel/cream. As an example, the use of topical tau-mag is contemplated to be as follows: a subject in need of topical tau-mag would collect about ⅛ to about ½ teaspoon of gel/cream either from a tube of topical tau-mag or from a jar of topical tau-mag on a suitable device and apply it to an affected area of the body. The affected area can be the face, parts of the neck, chest, and back, and/or other affected bodily areas.

Treatment compositions based on nanoparticles are under investigation as novel treatments of acne vulgaris and other skin lesions. Because of their unique physical properties, including their high surface area to size ratio, nanoparticles are ideal for use in various skin care products currently on the market because of their ability for enhanced mobility within any environment in the body. The benefits, side-effects and long-term consequences of using nanoparticles in therapeutic and/or cosmetic compositions are currently being actively explored (Wiesenthal A et al., International Journal of Dermatology, March; 50(3):247-54 (2011)).

Thus, in some embodiments, the composition may be topically delivered using nanoparticles. The nanoparticles comprise those that can be used for dermatological purposes. In some embodiments, nanoparticles can be used for topical spot treatment of, without limitation, one or more of mild/sporadic or break-out lesions, acute impending lesions or severe acne.

It is understood in the art that an active ingredient in a composition may require a different vehicle for optimized therapy depending on the concentration of the active ingredient used for therapy. Therefore, one of ordinary skill in the art may decide which vehicle to use on a case by case basis. An example of inactive ingredients in a topical composition may comprise carbomer (gelling agent), purified water (solvent), potassium sorbate (preservative), propylene glycol (permeation enhancer). Additional examples of excipients in topical formulations can be found in Chang et al., The AAPS Journal, 15:41-52 (2013), which is hereby incorporated by reference in its entirety. In some embodiments, the inactive ingredients may be selected from acrylates copolymer, carbomer 940, docusate sodium, edetate disodium, glycerin, poloxamer 182, propylene glycol, purified water, silicon dioxide, sodium hydroxide. In another variation, inactive ingredients in a topical composition may comprise carbomer, disodium EDTA, hydroxypropyl methylcellulose, laureth-4, sodium hydroxide, water. Additional examples of topical formulations can be found in Raphael et al., Therapeutic Delivery, February 6, 2:197-216 (2015), which is hereby incorporated by reference in its entirety.

Oral Compositions Comprising Taurine and Magnesium

In some embodiments an oral composition is provided. In some embodiments, the oral composition comprises taurine and magnesium. The oral composition may be referred to herein as "oral tau-mag." In some embodiments, the "oral tau-mag" is an oral supplement comprising high-dose taurine and low-dose magnesium. In some embodiments, the oral composition comprises a high dose of taurine. The magnesium in tau-mag may be magnesium citrate, magnesium chloride, magnesium oxide or some other form of magnesium. In some embodiments, the dose of taurine is about 3 g per day. In some embodiments, the dose of taurine is from about 0.5 to about 6 g per day. In some embodiments, the dose of taurine is equal to about 0.5, 1, 1.5, 2, 2.5, 3, 3.5, 4, 4.5, 5, 5.5 or 6 g per day or within a range defined by any two of the aforementioned values. The dose of taurine in the oral composition may be greater than about 0.1 g per day and less than about 20 g per day. In another variation, the oral supplement is a tablet or a capsule or a powder comprising taurine in a range of about 500 to about 1500 mg per capsule or per tablet or per unit dose of powder. In some embodiments, the oral composition additionally comprises a low dose of magnesium. In some embodiments, the dose of magnesium is about 200 mg per day. In some embodiments, the dose of magnesium is from about 25 to about 500 mg per day. In some embodiments, the dose of magnesium is equal to about 25, 50, 100, 150, 200, 250, 300, 350, 400, 450 or 500 mg per day or within a range defined by any two of the aforementioned values.

The dose of magnesium in the oral composition may be greater than about 1 mg per day and less than about 1 g per day. In another variation, the oral supplement is a tablet or a capsule or a powder comprising magnesium in a range of about 50 to about 150 mg per capsule or per tablet or per unit dose of powder. In some embodiments, the oral composition is taken for about 1 day to about 21 days. In some embodiments, the oral composition is taken for 1, 2, 3, 4, 5, 6, 7, 8, 9, 10, 11, 12, 13, 14, 15, 16, 17, 18, 19, 20 or 21 days or within a range defined by any two of the aforementioned values. In some embodiments, the oral composition is taken for about 1 to about 52 weeks. In some embodiments, the oral composition is taken for 4, 5, 6, 7, 8, 9, 10, 11, 12, 13, 14, 15, 16, 17, 18, 19, 20, 21, 22, 23, 24, 25, 26, 27, 28, 29 or 30 weeks or within a range defined by any two of the aforementioned values.

In some embodiments, the oral composition is taken as divided doses per day. In some embodiments, the oral composition is taken as about 2 to about 12 divided doses per day. In some embodiments, the oral composition is taken as 2, 3, 4, 5, 6, 7, 8, 9, 10, 11 or 12 divided doses per day or within a range defined by any two of the aforementioned values. In some embodiments, the oral composition is taken as multiple doses per day. In some embodiments, the oral composition is taken as about 2 to about 12 multiple doses per day. In some embodiments, the oral composition is taken as 2, 3, 4, 5, 6, 7, 8, 9, 10, 11 or 12 multiple doses per day or within a range defined by any two of the aforementioned values. In some embodiments, the age of the subject is from about 10 to about 70 years. In some embodiments, the age of the subject is 10, 15, 20, 25, 30, 35, 40, 45, 50, 55, 60, 65 or 70 years or within a range defined by any two of the aforementioned values. In some embodiments, the age of the subject is lower than about 10 years. In some embodiments, the age of the subject is higher than about 70 years. In some embodiments, the sex of the subject is a male. In some embodiments, the sex of the subject is a female. In some embodiments, the subject has had acne for about 1 day. In some embodiments, the subject has had acne for less than 5 years. In some embodiments, the subject has had acne for about 5 years. In some embodiments, the subject has had acne for more than about 5 years. In some embodiments, the weight of the subject is from about 100 to about 250 lbs. In some embodiments, the weight of the subject is lower than about 100 lbs. In some embodiments, the weight of the subject is higher than about 250 lbs.

In some embodiments, the subject has not tried other acne remedies. In some embodiments, the subject has tried other acne remedies. In some embodiments, the subject has unsuccessfully tried other acne remedies. In some embodiments, the relief from acne from other remedies was less than about 50%. In some embodiments, the relief from acne from other remedies was about 5 to about 50%. In some embodiments, the relief from acne from other remedies was equal to about 5, 10, 15, 20, 25, 30, 35, 40, 45 or 50% or within a range defined by any two of the aforementioned values.

In some embodiments, the relief from acne from "oral tau-mag" was about 80 to about 100%. In some embodiments, the relief from acne from "oral tau-mag" was equal to about 80, 85, 90, 91, 92, 93, 94, 95, 96, 97, 98, 99 or 100% or within a range defined by any two of the aforementioned values.

Oral tau-mag may mitigate scars due to acne. Oral tau-mag may mitigate scars due to mild acne. Oral tau-mag may mitigate scars due to moderate acne. Oral tau-mag may mitigate scars due to severe acne. Scarring from acne may be reduced by about 20% to about 80% by topical tau-mag. Scarring from acne may be reduced by about 20, 25, 30, 35, 40, 45, 50, 55, 60, 65, 70, 75 or 80% by topical tau-mag or within a range defined by any two of the aforementioned values.

In some embodiments, the oral composition additionally comprises other micronutrients such as vitamins. In some embodiments, the oral composition additionally comprises other micronutrients such as minerals. In some embodiments, the oral composition additionally comprises other vitamins and minerals. In some embodiments, the oral composition additionally comprises one or more micronutrients, wherein the one or more micronutrients is selected from the group consisting of vitamin A, vitamin B1, vitamin B2, vitamin B3, vitamin B5, vitamin B6, vitamin B12, vitamin C, vitamin D, vitamin E, vitamin K, Folic Acid, Biotin, Calcium, Iron, Phosphorous, Iodine, Potassium, Zinc, Selenium, Manganese, Copper, Choline, Inositol, Omega 3 fatty acids, Lycopene, Lutein and Zeaxanthin.

In some embodiments, the subject has mild acne. In some embodiments, the subject has moderate acne. In some embodiments, the subject has severe acne. In some embodiments, the subject has mild-moderate acne. In some embodiments, the subject has moderate-severe acne. In some embodiments, "oral tau-mag" is partially effective. In some embodiments, "oral tau-mag" is about 80 to about 99% effective. In some embodiments, "oral tau-mag" is 80, 85, 90, 91, 92, 93, 94, 95, 96, 97, 98 or 99% effective or within a range defined by any two of the aforementioned values. In some embodiments, "oral tau-mag" is fully effective. In some embodiments, "oral tau-mag" is about 100% effective.

In some embodiments, oral supplements comprising high-dose taurine (about 3 g per day) together with low-dose magnesium (about 200 mg per day) can be very effective against mild-moderate acne, and can be partially effective against severe acne.

In some embodiments, oral supplementation with high-dose taurine oral supplementation (about 3 g per day, in divided doses) in combination with low-dose magnesium (about 200 mg magnesium per day, in divided doses) improves mild-moderate acne about 90 to about 100% within about 4 to about 12 weeks in adults.

In some embodiments, "oral tau-mag' is a formulation such as a capsule, caplet, tablet, other pill form, or powder. A subject in need of the formulation can take about 0.25-about 12 unit doses per day. The unit dose can be taken as a single dose or can be taken as a divided dose. The active ingredients of the formulation are a high dose of taurine and a low dose of magnesium. In some embodiments, each unit dose of the formulation comprises between about 200 mg to about 2 g taurine and about 50 mg to about 150 mg magnesium. The dose of taurine may be about 3 g per day. In some cases, the dose of taurine may range from about 0.5 to about 6 g per day. In some embodiments, the dose of taurine is equal to about 0.5, 1, 1.5, 2, 2.5, 3, 3.5, 4, 4.5, 5, 5.5 or 6 g per day or within a range defined by any two of the aforementioned values. The dose of taurine in the oral composition may be greater than about 0.1 g per day and less than about 20 g per day. In all embodiments, the oral composition additionally comprises a low dose of magnesium. In some embodiments, the dose of magnesium is about 200 mg per day. In some embodiments, the dose of magnesium is from about 25 to about 500 mg per day. In some embodiments, the dose of magnesium is equal to about 25, 50, 100, 150, 200, 250, 300, 350, 400, 450 or 500 mg per day or within a range defined by any two of the aforementioned values. The dose of magnesium in the oral composition may be greater than about 1 mg per day and less than about 1 g per day. The dose of magnesium may be equal to about 25, 50, 100, 150, 200, 250, 300, 350, 400, 450 or 500 mg per day or within a range defined by any two of the aforementioned values.

In addition to the active ingredients, the formulation may have inactive ingredients, such as a coating of pills, coloring agents for capsules, etc. The coating may comprise standard coating ingredients such as magnesium stearate and cellulose. The coating may be such that it allows for a timed-release of the active ingredients. The formulation may be sold in a pharmaceutical/nutraceutical bottle.

It is understood in the art that an active ingredient in a composition may require a different vehicle for optimized therapy depending on the concentration of the active ingredient used for therapy. Therefore, one of ordinary skill in the art may decide which vehicle to use on a case by case basis. An example of inactive ingredients in an oral composition may comprise cellulose (stabilizer, thickener), magnesium stearate (flow agent), and silicon dioxide (glidant). Additional examples of excipients in oral formulations can be found in Dave, Drug Topics, Oct. 24, 2008, which is hereby incorporated by reference in its entirety. Additional examples of oral formulations can be found in Mitragotri et al., Nature Reviews Drug Discovery, 13:655-672 (2014), which is hereby incorporated by reference in its entirety.

Additional Embodiments

In some embodiments, an anti-acne kit is provided. The anti-acne kit may comprise only topical tau-mag. The kit may comprise only oral tau-mag. In another variation, the kit may comprise both topical tau-mag and oral tau-mag. The kit may contain topical tau-mag and an oral supplement comprising various other micronutrients such as vitamins and minerals that may aid in effectiveness of taurine and magnesium against acne. The kit may contain oral tau-mag and an oral supplement comprising various other micronutrients such as vitamins and minerals that may aid in effectiveness of taurine and magnesium against acne. The kit may comprise topical tau-mag, oral tau-mag and an oral supplement comprising various other micronutrients such as vitamins and minerals that may aid in effectiveness of taurine and magnesium against acne. In some embodiments, the kit may comprise enough topical tau-mag and oral tau-mag to provide an average user with about 2-16 weeks of treatment.

The main reason to provide a kit of topical tau-mag and oral tau-mag that additionally comprises oral supplements from among an assortment of other micronutrients is to help prevent micronutrient deficiencies that could interfere with treatment of the skin. Most micronutrients are known to have effects on the skin, so trying to ensure that the skin obtains adequate levels of such micronutrients could potentially help with the ability of topical tau-mag and oral tau-mag to heal or prevent acne. Thus, in some embodiments, a kit is provided that comprises topical tau-mag and oral tau-mag, and additionally comprises oral supplements from among an assortment of other micronutrients, in order to help prevent micronutrient deficiencies that might interfere with treatment of the skin. Most micronutrients are important for some aspect of skin health, such as the healing of lesions. And certain micronutrients appear to support the specific functions of taurine and magnesium in the pilosebaceous units. For example, vitamins D and A appear to facilitate taurine transport across cell membranes; choline helps to maintain the correct size and shape of the lipid droplets, which may be necessary for magnesium to effectively catalyze their smooth breakup to microdroplets. Since a deficiency in such supportive micronutrients could hinder the ability of taurine and magnesium to adequately perform their functions in the pilosebaceous units, supplementation with these micronutrients during tau-mag treatment may aid in the reduction or prevention of acne. The oral supplements of additional micronutrients for the kit could resemble a standard multivitamin/mineral supplement, with doses selected to achieve optimal skin health or to best complement the taurine and the magnesium.

The oral supplement of micronutrients may additionally comprise micronutrients such as vitamins and/or minerals. The micronutrients are selected from the group consisting of vitamin A, vitamin B1, vitamin B2, vitamin B3, vitamin B5, vitamin B6, vitamin B12, vitamin C, vitamin D, vitamin E, vitamin K, Folic Acid, Biotin, Calcium, Iron, Phosphorous, Iodine, Potassium, Zinc, Selenium, Manganese, Copper, Choline, Inositol, Omega 3 fatty acids, Lycopene, Lutein and Zeaxanthin.

In some embodiments, an oral treatment or a topical treatment of a neonate or an infant who has acne is provided. The oral or topical treatment may be used for prevention of acne in the neonate or the infant. The oral or topical treatment has a high dose of taurine and a low dose of magnesium. In some embodiments, the age of the neonate or the infant can range from about 1 day to about 2 years. The neonate or the infant can be a male. The neonate or the infant can be a female. In some embodiments, the neonate or the infant has had acne for about 1 day. The neonate or the infant may have had acne for about 2 years.

The weight of the neonate or the infant may range from about 2 to about 15 lbs. The weight of the neonate or the infant may be lower than about 2 lbs. The weight of the neonate or the infant may be higher than about 15 lbs.

In the oral or topical treatment for a neonate or an infant, the dose of taurine is about 0.15 g per day. In some cases, the dose of taurine may range from about 0.05 to about 0.6 g per day. In some embodiments, the dose of taurine is equal to about 0.05, 0.1, 0.15, 0.2, 0.25, 0.3, 0.35, 0.4, 0.45, 0.5, 0.55 or 0.6 g per day or within a range defined by any two of the aforementioned values. The dose of taurine in the oral composition may be greater than about 0.01 g per day and less than about 2 g per day. In all embodiments, the oral composition additionally comprises a low dose of magnesium. In some embodiments, the dose of magnesium is about 50 mg per day. In some embodiments, the dose of magnesium is from about 6.25 to about 125 mg per day. In some embodiments, the dose of magnesium is equal to about 6.25, 12.5, 25, 37.5, 50, 62.5, 75, 87.5, 100, 112.5 or 125 mg per day or within a range defined by any two of the aforementioned values. The dose of magnesium in the oral composition may be greater than about 0.25 mg per day and less than about 0.25 g per day. The oral composition for the neonate and/or infant may be an oral supplement, for example a special baby formula with tau-mag for oral consumption specifically for baby acne. In some embodiments, the oral composition is taken for about 1 day to about 21 days. In some embodiments, the oral composition is taken for 1, 2, 3, 4, 5, 6, 7, 8, 9, 10, 11, 12, 13, 14, 15, 16, 17, 18, 19, 20 or 21 days or within a range defined by any two of the aforementioned values. In some embodiments, the oral composition is taken for about 1 to about 52 weeks. In some embodiments, the oral composition is taken for 4, 5, 6, 7, 8, 9, 10, 11, 12, 13, 14, 15, 16, 17, 18, 19, 20, 21, 22, 23, 24, 25, 26, 27, 28, 29 or 30 weeks or within a range defined by any two of the aforementioned values.

In some embodiments, an oral treatment or a topical treatment of a pre-teen is provided. The oral or topical treatment may be used for prevention of acne in the pre-teen. The oral treatment has a high dose of taurine and a low dose of magnesium. In some embodiments, the age of the pre-teen can range from about 2 years to about 12 years. The pre-teen can be a male. The pre-teen can be a female. The pre-teen may have had acne for about 1 day. The pre-teen may have had acne for about 2 years. The weight of the pre-teen may range from about 30 to about 70 lbs. The weight of the pre-teen may be lower than about 30 lbs. The weight of the pre-teen may be higher than about 70 lbs.

In the oral or topical treatment for a pre-teen, the dose of taurine is about 1.5 g per day. In some cases, the dose of taurine may range from about 0.5 to about 6 g per day. In some embodiments, the dose of taurine is equal to about 0.5, 1, 1.5, 2, 2.5, 3, 3.5, 4, 4.5, 5, 5.5 or 6 g per day or within a range defined by any two of the aforementioned values. The dose of taurine in the oral composition may be greater than about 0.1 g per day and less than about 20 g per day. In some embodiments, the oral composition additionally comprises a low dose of magnesium. In some embodiments, the dose of magnesium is about 200 mg per day. In some embodiments, the dose of magnesium is from about 25 to about 500 mg per day. In some embodiments, the dose of magnesium is equal to about 25, 50, 100, 150, 200, 250, 300, 350, 400, 450 or 500 mg per day or within a range defined by any two of the aforementioned values. The dose of magnesium in the oral composition may be greater than about 1 mg per day and less than about 1 g per day. In some embodiments, the oral composition is taken for about 1 day to about 21 days. In some embodiments, the oral composition is taken for 1, 2, 3, 4, 5, 6, 7, 8, 9, 10, 11, 12, 13, 14, 15, 16, 17, 18, 19, 20 or 21 days or within a range defined by any two of the aforementioned values. In some embodiments, the oral composition is taken for about 1 to about 52 weeks. In some embodiments, the oral composition is taken for 4, 5, 6, 7, 8, 9, 10, 11, 12, 13, 14, 15, 16, 17, 18, 19, 20, 21, 22, 23, 24, 25, 26, 27, 28, 29 or 30 weeks or within a range defined by any two of the aforementioned values.

In some embodiments, any of the oral and/or topical compositions provided herein may comprise one or more analgesic, anti-pyretic or anti-histaminic agents.

In some embodiments, any of the oral and/or topical compositions provided herein may be used as a cosmetic composition for treating one or more dysfunctional pilosebaceous units.

In some embodiments, any of the oral and/or topical compositions provided herein may be used as a cosmetic composition in a cosmetic method for treating one or more dysfunctional pilosebaceous units.

In some embodiments, any of the topical compositions provided herein may be formulated as a nanoparticle-based cosmetic composition for cosmetically treating one or more dysfunctional pilosebaceous units. The one or more nanoparticles efficiently deliver the effective amounts of taurine and magnesium, sufficient in combination, to the one or more dysfunctional pilosebaceous units.

In some embodiments, any of the topical compositions provided herein may be may be used as a nanoparticle-based cosmetic composition in a cosmetic method for cosmetically treating one or more dysfunctional pilosebaceous units. The one or more nanoparticles efficiently deliver the effective amounts of taurine and magnesium, sufficient in combination, to the one or more dysfunctional pilosebaceous units.

In some embodiments, the nanoparticle can be of zinc oxide, titanium dioxide, gold, silver, platinum, etc. In some embodiments, the nanoparticles can be shaped like nanoplates, rods, shells, wires, prisms, spheres, ovoids, pyramids, cylinders, spirals, cubes, cubiods, ellipsoids, etc. In some embodiments, the nanoparticles can be amorphous.

In some embodiments, the efficiency a nanoparticle-based composition for cosmetically treating one or more dysfunctional pilosebaceous units may be about 75% to about 100% better than of a composition that is not nanoparticle-based. In some embodiments, the efficiency a nanoparticle-based composition for cosmetically treating one or more dysfunctional pilosebaceous units may be about 50, 55, 60, 65, 70, 75, 80, 85, 90, 95, 100, 105, 110, 115, 120, 125, 130, 135, 140, 145 or 150% better than of a composition that is not nanoparticle-based or within a range defined by any two of the aforementioned values.

The standard suggested daily dose of topical tau-mag or oral tau-mag is a safe dose, consisting of an amount of taurine that does not exceed the upper observed safe level that has been reported in the scientific literature, and an amount of magnesium that does not greatly exceed the recommended daily allowance.

EXAMPLES

The following non-limiting examples show Study Volunteer experiences with various taurine-magnesium treatment regimens. Volunteers were listed in the chronological order of the start of their taking full daily doses of taurine with magnesium.

Severity of acne was the following: Volunteers 1 and 2 had sporadic mild acne, Volunteers 3 and 4 had chronic cyclic mild acne, Volunteer 5 had chronic acne that appeared to be between mild and moderate, Volunteer 6 had chronic severe acne with scarring, Volunteer 7 had chronic moderate acne, Volunteer 8 had frequent mild acne, and Volunteer 9 had acne that appeared to be between mild and moderate. The oral tau-mag treatments used in the following examples appear to be very safe: 6 of the Volunteers experienced no side effects at all, and 3 Volunteers reported very mild side effects for the first 2 weeks of treatment only, such as burping or gas.

Example 1

Volunteer 1: Female, age 54, height 5'3", weight 105 lbs.
Treatment Regimen: Volunteer 1 initially took taurine supplements (500 mg daily) for nutritional reasons, without knowing that taurine might have any prophylactic or healing effect on acne. One taurine dose per day was taken with a multivitamin/mineral pill, which contained 50 mg magnesium. Volunteer 1 had been experiencing sporadic breakouts of very mild acne, which stopped with the addition of taurine with the multivitamin/mineral pills, with the exception of one small lesion months later that was cleared in 3 days with a stepped-up dose of 1 g of taurine/day with the multivitamin/mineral pill. Subsequently, acute hints of an impending acne lesion were mitigated within 1-3 days with a short-term dose of 1.5 g/day taurine combined with 200 mg/day magnesium oxide (or 150 mg magnesium oxide in vitamin/mineral pills). Taurine dose was very important: 1.5 g taurine was much more effective than 500 mg for acute problems. The reason that Volunteer 1 was responsive to a taurine dose as low as 500 mg to 1.5 g may have been related to the age-related decrease in monthly hormonal fluctuations that can influence acne. In summary, taurine with magnesium (or with multivitamin/mineral pills that contain magnesium) completely cured and continues to prevent acne in Volunteer 1.

Result: Excellent. Complete sustained clearing of mild acne.

Example 2

Volunteer 2: Female, age 50, height 5'5", weight 133 lbs.
Treatment Regimen: Recommendation initially was for daily taurine of 1.5 g in 3 divided doses, without magnesium. After 5 days the treatment was switched to 2 g/day taurine with multivitamin/mineral pills containing a total of 150 mg magnesium oxide, in divided doses. Volunteer 2 had experienced only occasional acne in adulthood, but in recent months she had been experiencing frequent mild breakouts, with lesions few in number but very noticeable. At the time of treatment Volunteer 2 had 3 significant acne lesions. Although there was no improvement after 5 days of taurine alone, after 7 days on the combined taurine-magnesium (with multivitamin/mineral) treatment, the Volunteer's skin was beautifully clear, so she stopped treatment, other than occasional low doses for the purpose of overall skin health, and has remained free of acne for 2 years.

Result: Excellent. Complete clearing of mild acne, even after treatment ended.

Example 3

Volunteer 3: Female, age 29, height 5'3", weight 118.
Treatment Regimen: Initial recommendation was for daily 1.5 g taurine (in divided doses, 1 g and 500 mg) with 200 mg magnesium oxide taken with the first daily taurine dose. Volunteer 3 typically had menstrual acne, starting the week before her period, with lesions few in number but often deep and bothersome, and she sometimes had acne during other parts of her cycle. After 4 days of taurine-magnesium treatment coinciding with menstrual acne, Volunteer 3 stopped treatment temporarily and resumed treatment after about 2 weeks, during mid-cycle. She opted then to take each taurine dose with a multivitamin/mineral pill containing magnesium oxide (total magnesium oxide daily was 100 mg). She cleared completely and stayed clear throughout her next menstrual period. About a week after her period ended, she stopped taurine-magnesium treatment, and her skin stayed beautifully clear for another week before showing some acne again. Even though her taurine-magnesium treatment was of short duration, her acne after treatment became so light over the next 21 months that she was usually clear. The results of her short treatment appear to be excellent and effective long-term.

Result: Excellent. Complete clearing of mild acne for duration of menstrual cycle while on treatment, then long-term cessation of most acne activity even without further treatment.

Example 4

Volunteer 4: Female, age 27, height 5'10", weight 164 lbs.
Treatment Regimen: Initial recommendation was for daily 1.5 g taurine (a low dose for the Volunteer's weight) with 200 mg magnesium oxide. Volunteer 4 had experienced mild acne during teenage years, and then again during adult years after getting off birth control pills a few years ago. Although usually her acne was very mild, she was especially prone to pronounced acne lesions during her menstrual periods and the week before each period. She had not had completely clear skin in years. For the first week, Volunteer 4 took taurine only, with slight improvement. For the next couple of weeks Volunteer 4 complied only sporadically with her treatment regimen. After she started taking her doses consistently, her acne reduced rapidly over several days, but without quite clearing completely, and then it returned with the approach of her menstrual period. Therefore, the recommended dose was increased to 2 g taurine daily (still low for her weight), and the form of magnesium was switched to 150 mg magnesium citrate (more soluble and bioavailable than magnesium oxide). Nine days later, Volunteer 4 reported that her skin was the clearest it had been in over a year, but she subsequently experienced break-outs after consecutive days of poor compliance. Upon resuming full treatment, her skin cleared rapidly and completely, for the first time in years. She broke out slightly during her next period, and then had inconsistent compliance for a couple of weeks. She resumed full doses and within a week cleared completely, even though she was on her menstrual period for part of that time. Two weeks later Volunteer 4 reported that she had stayed on her regular dose of taurine with magnesium and had very clear skin. Shortly thereafter, Volunteer 4 stopped treatment in preparation for pregnancy. Thus, no conclusions can be drawn with respect to whether or not she would have stayed clear throughout consecutive menstrual cycles.

Result: Very good. Complete clearing of mild acne.

Example 5

Volunteer 5: Male, age 26 (started treatment at age 25), height 5'9", weight 150 lbs.
Treatment Regimen: Initial recommendation was for daily 2 g taurine with 200 mg magnesium oxide in divided doses. Volunteer 5 had had an acne problem since teenage years. His degree of acne seemed worse than mild because many of his acne lesions had an unusual appearance, starting out as flat bright red spots, roughly ¼-½ cm in diameter, which days or weeks later erupted into acne lesions that were often deep. After 17 days taking 2 g taurine with 200 mg magnesium citrate daily, he continued to break out, although the lesions were less deep and did not last as long. The treatment dose was then increased to 3 g/day taurine and 200 mg/day magnesium citrate. Within 3 days, very good clearing was achieved. The acne was reduced to the remnants of 4 lesions, and the Volunteer looked much better than when he began treatment. Two weeks later his skin was clearer, although not completely clear. After several months of taking taurine-magnesium inconsistently, he reported that whereas a dose of 3 g of taurine with magnesium was very effective against his acne, a dose of 2 g of taurine with magnesium was slow to clear it. After a few more months, he stopped taking taurine-magnesium, even though he had experienced good clearing and no side effects, because he disliked the inconvenience of having to remember to take pills 3 times a day. In summary, the Volunteer's skin was very sensitive to changes in taurine dose, breaking out easily when doses were missed. When he took his full doses of taurine-magnesium for a couple of consecutive weeks, however, he improved by about 90%.

Result: Good. About 90% improvement was observed of acne that appeared to be mild to moderate.

Example 6

Volunteer 6: Female, age 24, height 5'3", weight 155 lbs.

Treatment Regimen: Initial treatment regimen was 3 g taurine with 200 mg magnesium. The Volunteer had severe acne, which had started with blemishes at age 10 or 11. Scarring on her cheeks was extensive, with many pitted scars. Her cheeks, jaw-line, and upper neck area looked very swollen and bumpy, likely indicating substantial acne beneath the skin surface, and these areas were prone to deep long-lasting acne lesions. The Volunteer had tried various anti-acne products over the years, but none had worked for her. Within the first 2 weeks of taurine-magnesium treatment, the Volunteer noticed that the duration of lesions was shorter and that the indentation of scars seemed less deep than before. At this time, it was recommended that the Volunteer also take a daily multivitamin/mineral pill to prevent common micronutrient deficiencies that could interfere with treatment. Over the next 2 weeks, the Volunteer experienced significant improvement: swelling of the main acne areas greatly decreased, noticeably changing the shape of her face, especially in the lower cheeks and along the jaw-line; the texture of her skin was smoother; and most lesions were smaller. Over the subsequent 3 weeks, the swelling of her inflamed acne areas continued to decrease, and most of the redness of her cheeks disappeared; although she had a couple of pronounced new acne lesions, the old lesions were either gone or had flattened, and new lesions tended to be of much shorter duration. She looked about 10 years younger than at the start of treatment, and her overall improvement appeared to be about 75%. However, in the following week the Volunteer experienced no improvement, and in the week following that, she experienced a partial reversal: the main acne-prone areas began swelling again and breaking out, but not as badly as before treatment. Over the next 3 weeks her degree of swelling fluctuated, and her neck area had many red flat lesions. It was recommended that she stop taking the multivitamin/mineral pill because it contained a large amount of vitamin B-12, and there are reports that high doses of vitamin B-12 sometimes lead to acne. Over the next few months her condition continued to fluctuate, with the main problem near the jaw-line and neck, although she still looked better than before treatment. During these months she was recommended to try lecithin (phosphatidylcholine) for a few weeks, for lipid droplet stabilization in interacting with the magnesium; she was also recommended the RDA of zinc, to facilitate taurine utilization by cells, even though she had tried zinc for acne unsuccessfully prior to starting taurine-magnesium treatment. Approximately 6 months after her improvement started reversing, the Volunteer improved again to around the 75% level, as the acne activity along the jaw-line and on the neck became low, although her condition fluctuated from week to week. She continued taking zinc, but not lecithin. Months later she was recommended to start taking vitamin D daily to enhance taurine transport across cell membranes. At last report, a couple of months later, the Volunteer was doing very well on taurine-magnesium treatment, at around the 85% improvement level. Her remaining acne was mild, and scarring was greatly mitigated. She looked very different from the way she looked at the start of treatment, with a normal jaw-line that was no longer hugely swollen with acne, even though she had not lost any weight during her treatment to account for the change in facial features. For someone with severe acne, a higher treatment dose could be investigated.

Result: Fairly good improvement. Severe acne improved, eventually to about the 85% level, resulting in a dramatic beneficial alteration in her facial appearance.

Example 7

Volunteer 7: Male, age 20, height 5'11", weight 170 lbs.

Treatment Regimen: Initial recommendation for the Volunteer was for daily 3 g taurine with 200 mg magnesium citrate, in divided doses. The recommendation after week 2, in addition to the taurine-magnesium, was for a multivitamin/mineral with lunch. The Volunteer's degree of acne was moderate, with numerous acne bumps on the forehead and cheeks as well as some large blemishes on the forehead, both sides of the face, and the upper neck. He had experienced acne continuously for 5 years, and he had used an over-the-counter acne product after the first year that seemed to significantly worsen his acne. It was reported that 4 months prior to taurine-magnesium treatment, the Volunteer's acne had been more severe. In the first 2 weeks of taurine-magnesium treatment, the Volunteer's face noticeably began to clear. Over the next 2 weeks, his acne bumps and old lesions were reduced in depth and number, new lesions were superficial rather than deep, and the redness of his complexion disappeared. Over the next 4 weeks his skin cleared to over 90% improvement, as the acne bumps were virtually gone, and most of the remaining lesions were just flat red dots. At that time it was recommended that the Volunteer stop taking the multivitamin/mineral because it had a high level of vitamin B-12 that could possibly induce an acne flare-up. Over the next 6 weeks, new lesions were not very noticeable and usually cleared within days, and scars continued to fade. By the end of week 15, the Volunteer's skin was completely clear. The Volunteer began taking zinc at 25 mg every other day to help with taurine utilization. He frequently experienced very minor breakouts that cleared quickly. Over the next half-year his skin condition fluctuated around the 95% improvement level. He then decreased his taurine dose to a maintenance dose of 2 g daily and stayed at about the same level of improvement for about 4 months, before clearing completely for several weeks at last report. Of note also is that a few months into his treatment his depression lifted.

Result: Very good. Moderate acne of 5 years' duration cleared completely in 15 weeks, with only minor lesions appearing sporadically in the following weeks.

Example 8

Volunteer 8: Male, age 28, height 5'8", weight 165 lbs.

Treatment Regimen: Initial recommendation was for 2 g/day taurine with 200 mg/day magnesium in 2 divided doses for the first week, and for 3 g/day taurine with 200 mg/day magnesium for the second week and thereafter. The Volunteer usually experienced at least very mild acne, with non-superficial lesions mainly restricted to the beard area, and recently his acne had worsened, making shaving in the chin area uncomfortable. At the end of the first week the Volunteer showed noticeable improvement, with a clearing of the few lesions from the sides of his face. At the end of week 2, the Volunteer had significant old and new lesions on the chin, but was clear otherwise, and he reported the hue of his skin being better. At the end of week 3, the Volunteer reported no significant change, and was recommended a daily multivitamin/mineral supplement in addition to taurine-magnesium. Two days later, Volunteer 8 reported that his chin lesions had diminished. By the end of week 4, the remaining lesions were flat and had almost disappeared. By the end of week 5, his acne had cleared completely.

Result: Excellent. Mild acne cleared completely in 5 weeks while on treatment.

Example 9

Volunteer 9: Female, age 22, height 5'6", weight 140 lbs.

Treatment Regimen: Volunteer 9 started with 3 g/day taurine and 300 mg/day magnesium, in 3 divided doses. The Volunteer had mild acne for a couple of years, which rapidly worsened when she moved to a residence dependent on reddish well-water with very high iron content. By the time the Volunteer started taurine-magnesium treatment 6 weeks later, her degree of acne seemed to be between mild and moderate. The most significant of her acne lesions were about a dozen pronounced raised lesions in the cheekbone areas. Clearing during the first 6 weeks of her taurine-magnesium treatment was good, with an overall improvement estimated by the Volunteer to be 70%, taking into account the number and depth of lesions. Then Volunteer 9 abruptly cut her dose to 2000 mg taurine and 200 mg magnesium and worsened considerably over 3 weeks until she resumed a taurine dose of 3000 mg, at which time she slowly improved over 10 weeks. Upon moving to a residence with clear water, she improved quickly and significantly with treatment within one week, to about the 90% level, and then ended treatment.

Result: Overall good but variable improvement, with degree of clearing apparently influenced by water quality.

A summary of the treatment regimens and treatment outcomes in the above 9 working examples is presented in the TABLE 1. The data provided in the Examples support the surprising conclusion that relatively high doses of taurine together with magnesium provide excellent treatment and in some cases prevention of mild to severe acne. TABLE 1 does not reflect all instances of all micronutrient supplements taken by the Volunteers. As described in the Examples, some Volunteers, in addition to taking their recommended supplements of taurine and magnesium, for some weeks or months took other micronutrient supplements or even a multivitamin/mineral supplement containing an extra low dose of magnesium. Where the volunteers complied with the recommended treatment regimen, all subjects experienced major improvement, with most enjoying from 90% to 100% clearing of their acne lesions.

TABLE 1

Summary of Treatment Observations

| | Treatment Presentation | TAU (mg/day) | Mg (mg/day) | Treatment Period | Treatment Outcome |
|---|---|---|---|---|---|
| Volunteer 1 | Mild/sporadic | 500 | 50 | >8 weeks | Lesion-free |
| | Break-out lesion | 1000 | 150 | 1-3 days | Lesion cleared |
| | Acute impending lesion | 1500 | 200 | 1-3 days | Lesion prevented |
| Volunteer 2 | Mild acne with | 1500 | 0 | 5 days | No improvement |
| | noticeable lesions | 2000 | 150 | 7 days | Lesions cleared |
| Volunteer 3 | Mild acne | 1500 | 100 | Almost 4 weeks | Lesion-free post-treatment mostly clear for next 21 months |
| Volunteer 4 | Mild acne | 1500 | 0 | 7 days | Slight improvement |
| | Break-out lesions with menstrual period | 1500 | 200 | >3 days | Improvement |
| | | 2000 | 150 | >3 weeks | Lesions cleared |
| Volunteer 5 | Acne in between mild and moderate | 2000 | 200 | 17 days | Slight improvement |
| | | 3000 | 200 | 3 days | Major improvement |
| | | 3000 | 200 | 2 weeks | 90% clear |
| Volunteer 6 | Severe acne | 3000 | 200 | 2 weeks | Slight improvement |
| | | | | 2 weeks | Significant improvement |
| | | | | 3 weeks | 75% clearing |
| | | | | 2 weeks | 40% clearing |
| | | | | 6 months | 75% clearing |
| | | | | 8 months | 85% clearing |
| Volunteer 7 | Moderate acne with noticeable deep lesions | 3000 | 200 | 13 weeks | 95% clear |
| Volunteer 8 | Mild acne | 2000 | 200 | 1 week | Improvement |
| | | 3000 | 200 | 4 weeks | Lesion-free |

TABLE 1-continued

Summary of Treatment Observations

|  | Treatment Presentation | TAU (mg/day) | Mg (mg/day) | Treatment Period | Treatment Outcome |
|---|---|---|---|---|---|
| Volunteer 9 | Acne in between mild and moderate | 3000 | 300 | 6 weeks | 70% clearing |
|  |  | 2000 | 200 | 3 weeks | No overall clearing |
|  |  | 3000 | 200 | 10 weeks | Improvement |
|  |  | 3000 | 200 | 1 week, with clear water | 90% clearing |

ADDITIONAL TREATMENT SCENARIOS

Scenario 1—Topical Spot Treatment for Mild/Sporadic or Break-out Lesions or Acute Impending Lesions The subject can present with mild/sporadic or break-out lesions or acute impending lesions. The subject may have had mild/sporadic or break-out lesions for 1 day to several days. A composition can be administered as a topical treatment. The topical treatment can be in the form of a gel or a cream. The composition is topically applied at the site of the mild/sporadic or break-out lesion or acute impending lesion. The topical treatment gel or cream comprises a combination of an amount of taurine and an amount of magnesium sufficient to treat mild/sporadic or break-out lesions or prevent acute impending lesions. The concentrations for taurine and magnesium in the spot treatment embodiments would be within the ranges given for taurine and magnesium in the other topical embodiments. For example, the amount of taurine can be about 500 mg per ½ teaspoon of the gel or the cream. The amount of magnesium can be about 100 mg per ½ teaspoon of the gel or the cream. Additionally, the topical treatment composition comprises a pharmaceutically acceptable carrier. The subject can apply the gel or the cream two to four times a day at the site of the mild/sporadic or break-out lesion or the acute impending lesion. The subject can apply the gel/cream for about 1 week. After 1 week of application of the gel or the cream, the mild/sporadic or break-out lesions may be cleared and the acute impending lesions prevented.

Scenario 2—Topical Spot Treatment for Severe Acne

The subject can present with severe acne. The subject may have had severe acne for several days to several months. A composition of the present disclosure can be administered as a topical treatment. The topical treatment can be in the form of a gel or a cream. The composition is topically applied at the site of severe acne. The topical treatment gel or cream comprises a combination of an amount of taurine and an amount of magnesium sufficient to treat the severe acne. Additionally, the topical treatment composition can comprise other therapeutic components such as an analgesic to reduce the pain associated with severe acne. Furthermore, the topical treatment composition comprises a pharmaceutically acceptable carrier. The concentrations for taurine and magnesium in the spot treatment embodiments would be within the ranges given for taurine and magnesium in the other topical embodiments. For example, the amount of taurine can be about 1000 mg per ½ teaspoon of the gel or the cream. The amount of magnesium can be about 150 mg per ½ teaspoon of the gel or the cream. The subject can apply the gel or the cream two to four times a day at the site of the mild/sporadic or break-out lesion or the acute impending lesion. The subject can apply the gel/cream for about 1-4 months. After 1-4 months of application of the gel or the cream, the severe acne may be significantly improved or cleared.

Scenario 3—Nanoparticle-based Topical Spot Treatment

The subject can present with severe acne. The subject may have had severe acne for several days to several months. The composition is a nanoparticle-based cosmetic composition for cosmetically treating one or more dysfunctional pilosebaceous units causing severe acne. The composition of the present disclosure can be administered as a topical treatment. The topical treatment can be in the form of a gel or a cream. The composition is topically applied at the site of severe acne. The topical treatment gel or cream can comprise gold nanoparticles shaped in the form of nanospheres that are coated with a combination of an amount of taurine and an amount of magnesium in a pharmaceutically acceptable carrier. The combination of an amount of taurine and an amount of magnesium is sufficient to treat the severe acne. Additionally, the topical treatment composition can comprise other therapeutic components such as an analgesic to reduce the pain associated with severe acne. The nanoparticles efficiently deliver the composition to the one or more dysfunctional pilosebaceous units causing severe acne. The concentrations for taurine and magnesium in the spot treatment embodiments would be within the ranges given for taurine and magnesium in the other topical embodiments. For example, the amount of taurine can be about 200 mg per ½ teaspoon of the gel or the cream. The amount of magnesium can be about 50 mg per ½ teaspoon of the gel or the cream. The subject can apply the gel or the cream once a day at the sites of severe acne. The subject can apply the gel/cream for about 1-2 weeks. After 1-2 weeks of application of the gel or the cream, the severe acne lesions may be significantly improved or cleared.

DEFINITIONS

As used herein, the section headings are for organizational purposes only and are not to be construed as limiting the described subject matter in any way. All literature and similar materials cited in this application, including but not limited to, patents, patent applications, articles, books, treatises, and internet web pages are expressly incorporated by reference in their entirety for any purpose. When definitions of terms in incorporated references appear to differ from the definitions provided in the present teachings, the definition provided in the present teachings shall control. It will be appreciated that there is an implied "about" prior to the temperatures, concentrations, times, etc discussed in the present teachings, such that slight and insubstantial deviations are within the scope of the present teachings herein.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

In this application, the use of the singular includes the plural unless specifically stated otherwise. Also, the use of "comprise", "comprises", "comprising", "contain", "contains", "containing", "include", "includes", and "including" are not intended to be limiting. It is to be understood that both the foregoing general description and the following detailed description are exemplary and explanatory only and are not restrictive. Unless defined otherwise, technical and scientific terms used herein have the same meaning as commonly understood by one of ordinary skill in the art to which this invention belongs.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one of skill in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

Although this invention has been disclosed in the context of certain embodiments and examples, those skilled in the art will understand that the present invention extends beyond the specifically disclosed embodiments to other alternative embodiments and/or uses of the invention and obvious modifications and equivalents thereof. In addition, while several variations of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. It should be understood that various features and aspects of the disclosed embodiments can be combined with, or substituted for, one another in order to form varying modes or embodiments of the disclosed invention. Thus, it is intended that the scope of the present invention herein disclosed should not be limited by the particular disclosed embodiments described above.

The terminology used in the description presented herein is not intended to be interpreted in any limited or restrictive manner. Rather, the terminology is simply being utilized in conjunction with a detailed description of embodiments of the systems, methods and related components. Furthermore, embodiments may comprise several novel features, no single one of which is solely responsible for its desirable attributes or is believed to be essential to practicing the inventions herein described.

What is claimed is:

1. A method for decreasing sebum in a subject in need thereof, the method comprising administering a combination comprising an effective amount of taurine and an effective amount of magnesium, thereby decreasing sebum in sebaceous glands, sebaceous ducts, or both of the subject, wherein the effective amount of taurine is about 500 mg to about 6000 mg per day and wherein the effective amount of magnesium is about 50 mg to about 500 mg per day.

2. The method of claim 1, wherein decreasing sebum in the sebaceous glands, sebaceous ducts, or both of the subject is achieved by inhibiting LXR-alpha-induced lipogenesis within the sebaceous glands by the effective amount of taurine.

3. The method of claim 1, wherein decreasing sebum in sebaceous glands, sebaceous ducts, or both of the subject is achieved by activating magnesium-activated protein kinase phosphorylation-induced breakdown of large lipid droplets within the sebaceous glands, sebaceous ducts, or both by the effective amount of magnesium.

4. The method of claim 1, wherein administering the combination is oral, topical, or both.

5. A combination comprising an effective amount of taurine and an effective amount of magnesium, wherein the effective amounts of taurine and magnesium decrease sebum in sebaceous glands, sebaceous ducts, or both of a subject, wherein the effective amount of taurine is about 500 mg to about 6000 mg per day and wherein the effective amount of magnesium is about 50 mg to about 500 mg per day.

6. The combination of claim 5, wherein the combination is administered orally, topically, or both.

7. The combination of claim 5, wherein the effective amounts of taurine and magnesium decrease sebum in sebaceous glands, sebaceous ducts, or both of the subject by inhibiting LXR-alpha-induced lipogenesis within the sebaceous glands by the effective amount of taurine.

8. The combination of claim 5, wherein the effective amounts of taurine and magnesium decrease sebum in sebaceous glands, sebaceous ducts, or both of the subject by activating magnesium-activated protein kinase phosphorylation-induced breakdown of large lipid droplets within the sebaceous glands, sebaceous ducts, or both by the effective amount of magnesium.

* * * * *